United States Patent [19]

Ali

[11] 4,252,659

[45] Feb. 24, 1981

[54] PROCESS FOR THE PRODUCTION OF OVERBASED MANGANESE SALTS OF ORGANIC ACIDS

[75] Inventor: Asghar Ali, Edison, N.J.

[73] Assignee: Tenneco Chemicals, Inc., Saddle Brook, N.J.

[21] Appl. No.: 84,259

[22] Filed: Oct. 12, 1979

[51] Int. Cl.$^3$ .................... C10M 1/40; C10M 1/24
[52] U.S. Cl. .................................. 252/33; 252/33.4; 252/35; 44/51
[58] Field of Search .................... 252/33, 35, 33.4; 44/51

[56] References Cited

U.S. PATENT DOCUMENTS

| | | | |
|---|---|---|---|
| 3,827,979 | 8/1974 | Piobowski et al. | 252/39 |
| 3,857,790 | 12/1974 | Saunders et al. | 252/33 |
| 4,179,385 | 12/1979 | Ali et al. | 252/33 |

*Primary Examiner*—Jacqueline V. Howard
*Attorney, Agent, or Firm*—Evelyn Berlow

[57] ABSTRACT

Solutions of overbased manganese salts of organic acids that contain at least 13% by weight of manganese are prepared by carbonating a reaction mixture that contains excess manganous oxide, an oil-soluble organic acid, a solvent system, a promoter, a copromoter, and a third promoter that is an alkanoic acid having 1 to 3 carbon atoms at 70°–120° C. at a pressure of 1 atmosphere to 10 atmospheres.

10 Claims, No Drawings

PROCESS FOR THE PRODUCTION OF OVERBASED MANGANESE SALTS OF ORGANIC ACIDS

This invention relates to a process for the production of overbased oil-soluble manganese salts of organic acids. More particularly, it relates to a process for the production of solutions of overbased manganese salts of organic acids that contain at least 13% by weight of manganese by the carbonation of a system that comprises manganous oxide, an oil-soluble organic acid, a solvent, a promoter, a copromoter, and a third promoter.

Overbased manganese salts of organic acids, which are compounds in which manganese is present in excess of the stoichiometric amount required to react with the acidic groups of the organic acids, are widely used as additives in liquid hydrocarbon fuels and in lubricants for interal combustion engines. The basicity of these additives counteracts the corrosive acidic compounds that are formed during the operation of the engines and inhibits the formation of deposits of soot, lacquer, and sludge in the engines. In addition, these additives act as smoke suppressants in the fuels and improve the detergency of the lubricants.

The overbased salts are commonly produced by a process in which a basic manganese compound, such as manganous oxide, is suspended in an inert solvent that contains an organic acid, and a reaction promoter, and an acidic gas, which is usually carbon dioxide, is passed through the suspension to reduce its basicity. This process produces a product in which the manganese compound is complexed or dispersed in the solvent. Modifications of this process have been disclosed in a number of patents. For example, in U.S. Pat. No. 2,695,910, Asseff et al. disclosed a process in which overbased metal salts are prepared by the reaction of an alkaline earth metal compound with an acidic compound, a promoter that is, e.g., a phenolic compound, and preferably 5 to 50 moles of water per mole of the alkaline earth metal compound. Piotrowski et al. taught in U.S. Pat. No. 3,827,979 that when organic acids are overbased with manganous oxide in a carbonation process both a promoter that may be an ammonium halide and a copromoter that may be an alkaline earth metal halide must be present in the system if a highly-overbased product is to be obtained. In copending application Ser. No. 902,464, which was filed on May 3, 1978, Ali et al. reported that the process disclosed by Piotrowski et al. takes place too slowly to be useful commercially and that it converts only a portion of the manganous oxide to a highly-overbased manganese salt. They taught that when the process disclosed by Piotrowski et al. is carried out in the presence of a small amount of water and at a pressure in the range of 1 atmosphere to 10 atmospheres, the conversion of mangnous oxide to overbased manganese salts takes place more quickly and efficiently. In addition to providing higher yields of overbased manganese salts, the Ali et al. process has the further advantages of requiring shorter reaction times and of consuming less carbon dioxide than does the process disclosed in U.S. Pat. No. 3,827,979. Both the Piotrowski et al. process and the Ali et al. process yield relatively dilute overbased manganese salt solutions which must be concentrated, for example, by distillation under subatmospheric pressure, to solutions of overbased manganese salt that contain at least 13% by weight of manganese and that are useful as additives for fuel oils and lubricants.

This invention relates to an improved process for the production of overbased manganese salts and of solutions of overbased manganese salts that contain at least 13% by weight of manganese.

In the process of this invention, a reaction mixture that comprises manganous oxide, an oil-soluble organic acid, a solvent system, a promoter, a copromoter, and a third promoter that is a lower alkanoic acid is contacted with carbon dioxide while it is maintained at a temperature in the range of 70° C. to 120° C. at a pressure in the range of 1 atmosphere to 10 atmospheres until the carbonation reaction has been completed and there is obtained a clear, fluid solution of an overbased manganese salt that contains 13% by weight or more of manganese.

In addition to providing high yields of overbased manganese salt solutions that contain 13% or more manganese without the use of a concentration step, this process has the further advantages of yielding these products in reaction times that are far shorter than those required by the processes of the prior art and of being more economical to operate than those processes.

The oil-soluble organic acids, promoters, copromoters, and solvent systems that are used in the practice of this invention include those that were disclosed by Piotrowski et al. in U.S. Pat. No. 3,827,979, which is incorporated herein by reference.

The organic acids that are used in the process of this invention are organic carboxylic acids and organic sulfonic acids that are oil soluble and that form manganese salts that are oil soluble. They are preferably aliphatic and cycloaliphatic monocarboxylic acids having 4 to 10 carbon atoms, aromatic monocarboxylic acids having 7 to 12 carbon atoms, and mixtures thereof. Examples of these preferred acids include butyric acid, valeric acid, hexanoic acid, heptanoic acid, n-octanoic acid, 2-ethylhexanoic acid, n-nonanoic acid, isononanoic acid, neononanoic acid, n-decanoic acid, neodecanoic acid, naphthenic acids, benzoic acid, toluic acid, tert.butylbenzoic acid, hydroxybenzoic acids, chlorobenzoic acids, chlorotoluic acids, and the like.

The relative amounts of manganous oxide and the organic acid used are not critical provided that a stoichiometric excess of manganous oxide is present. In most cases a 5% to 100% molar excess of manganous oxide is used.

The promoters that are used in the process of this invention include ammonium halides, ammonium nitrate, mono-, di-, and trialkylamine hydrochlorides, ammonium sulfide and ammonium peroxydisulfate. Among the useful copromoters are alkaline earth metal halides, aluminum chloride, and ferric chloride. The reaction mixture usually contains from 1% to 10% by weight of the promoter and from 1% to 10% by weight of the copromoter, based on the weight of manganous oxide in the reaction mixture. Excellent results have been obtained using 2% to 4% of ammonium chloride as the promoter and 4% to 8% of calcium chloride or barium chloride as the copromoter, based on the weight of manganous oxide in the reaction mixture.

The solvent system in which the carbonation reaction is carried out contains 10% to 90% by weight of an alcohol that may be an alkanol having 1 to 12 carbon atoms, an ether-alcohol having 2 to 12 carbon atoms, a glycol having 2 to 12 carbon atoms or a mixture thereof and 10% to 90% by weight of an inert organic solvent that is a hydrocarbon and/or a halogenated hydrocarbon. The solvent system preferably contains 25% to 40% by weight of an alcohol and 60% to 75% by weight of a hydrocarbon. Illustrative of the alcohols that can be used are methanol, ethanol, isopropanol, hexanol, 2-ethylhexanol, 2-ethyldecanol, methoxyethanol, ethoxyethanol, butoxyethanol, hexoxyethanol, methoxyethoxyethanol, ethoxyethoxyethanol, butoxyethoxyethanol, hexoxyethoxyethanol, ethylene glycol, propylene glycol, diethylene glycol, dipropylene glycol, and mixtures thereof. The inert organic solvents that can be used include benzene, toluene, xylene, chlorobenzene, chlorotoluenes, dichlorotoluenes, naphtha, hexane, petroleum ether, and kerosene. Best results have been obtained when the alcohol was methoxyethanol or methoxyethoxyethanol and the inert organic solvent was hi-flash naphtha that contained 9% $C_8$ alkylbenzenes, 83% $C_9$ alkylbenzenes, and 8% $C_{10}$ alkylbenzenes. The amount of the solvent system that is used is that which will yield an overbased manganese salt solution that contains from 13% to 20% by weight of manganese. Unlike the previously-known processes, which require that the reaction mixture contain at least 3 parts by weight of alcohol per part by weight of manganous oxide, the present process gives high yields of overbased manganese salts when the reaction mixture contains not more than 1.50 parts by weight of alcohol per part by weight of manganous oxide.

In the process of this invention, the reaction of manganous oxide with an oil-soluble organic acid to form overbased manganese salts is carried out in the presence of a promoter, a copromoter, and a third promoter that is an alkanoic acid having 1 to 3 carbon atoms, namely, formic acid, acetic acid, propionic acid, and mixtures thereof. The preferred third promoters are formic acid, acetic acid, and compounds that are capable of generating these acids under the conditions of the carbonation reaction, for example, ammonium formate, ammonium acetate, and dimethylamine formate. Optimum results have been obtained when the third promoter was either 90% formic acid or glacial acetic acid. The amount of the acid that is used is that which will promote the carbonation reaction and cause it to take place quickly and to give nearly quantitative yields of highly overbased manganese salts. As little as 0.5% by weight of a third promoter, based on the weight of the solvent system, will increase the rate at which the carbonation reaction takes place. Five percent or more of the third promoter can be used, but the use of these amounts generally does not result in a further increase in the reaction rate. The best rates of reaction and the highest yields of overbased manganese salts result when the reaction mixture contains from 1% to 2% by weight of a third promoter that is a lower alkanoic acid, based on the weight of the solvent system.

During the carbonation reaction, the reaction mixture that comprises manganous oxide, an oil-soluble organic acid, a promoter, a copromoter, a third promoter, and a solvent system is maintained at a temperature in the range of 70° C. to 120° C. and a pressure in the range of 1 atmosphere to 10 atmospheres. It is preferably maintained at a temperature in the range of 90° to 110° C. and a pressure in the range of 1.5 to 3.5 atmospheres.

When the carbonation reaction has been completed, the product is a low viscosity, easily-filtered overbased manganese salt solution that contains at least 13% by weight, and usually 13% to 20% by weight of manganese. After filtration, this solution can be used without purification or other treatment as a fuel oil additive or as a component of lubricants for internal combustion engines. Alternatively, it can be heated under subatmospheric pressure to distill off a portion of the solvent system and to increase its manganese content to 22% to 28% by weight.

The process of this invention may be carried out as a batch, semi-continuous, or continuous process.

The invention is further illustrated by the following examples. In these examples, all parts are parts by weight and all percentages are percentages by weight.

EXAMPLE 1

To a stainless steel autoclave were charged 59.0 parts of n-heptanoic acid, 69.0 parts of manganous oxide (77.2% Mn), 3.3 parts of 90% formic acid, 2.0 parts of ammonium chloride, 3.4 parts of calcium chloride, 152.0 parts of hi-flash naphtha, and 59.0 parts of 2-methoxyethoxyethanol.

The autoclave was sealed and purged twice with carbon dioxide to remove air from it. The reaction mixture was stirred and heated to 96°–102° C. while the pressure in the autoclave was maintained at 2 atmospheres by the addition of carbon dioxide as needed. After two hours, a vigorous reaction occurred as shown by a sharp exotherm and by rapid absorption of carbon dioxide.

The reaction mixture was maintained at 96°–102° C. and carbon dioxide was added to it at a rate sufficient to maintain the pressure at 2 atmospheres for 3 hours after the start of the exotherm.

The system was vented to the atmosphere, and a solution of 0.066 part of an antifoam agent (SAG-47) in 1.0 part of the product was added to the reaction mixture. The reaction mixture was then sparged with nitrogen at 93°–99° C. under subatmospheric pressure (15 inches Hg absolute) for 30 minutes, cooled to 65° C., treated with filter-aid, and filtered. There was obtained 344.3 parts of an overbased manganese heptanoate solution that contained 13.9% of manganese.

The autoclave and filter cake were washed with 40.0 parts of hi-flash naphtha.

The concentrated product was then diluted with a portion of the wash liquor to obtain 373 parts of an overbased manganese heptanoate solution that contained 13.0% of manganese and that had a Gardner-Holdt viscosity of <A-5 at 25° C. and A-4 at −15° C.

EXAMPLE 2

To a stainless steel autoclave were charged 59 parts of n-heptanoic acid, 59 parts of 2-methoxyethoxyethanol, 152 parts of hi-flash naphtha, 3.26 parts of 90% formic acid, 2.04 parts of ammonium chloride, 3.45 parts of calcium chloride, and 69 parts of manganous oxide (77.2% Mn).

The autoclave was sealed and purged twice with carbon dioxide to remove air from it. The reaction mixture was then stirred and heated at 95°–100° C. while the pressure in the autoclave was maintained at 2 atmospheres by the addition of carbon dioxide as needed. After 50 minutes, a vigorous reaction occurred, as shown by a sharp exotherm and a rapid absorption of carbon dioxide.

The reaction mixture was maintained at 95°–100° C. and carbon dioxide was added at a rate that would maintain the pressure at 2 atmospheres until the carbonation reaction had been completed, as shown by an increase in the pressure in the autoclave.

The reaction product was cooled to 65° C., treated with filter-aid, and filtered. There was obtained an overbased manganese heptanoate solution that contained 13.8% of manganese in a yield of 95.8%, based on the weight of manganese oxide charged, with 256%-overbasing.

EXAMPLE 3

To a stainless steel autoclave were charged 33 parts of n-heptanoic acid, 41 parts of 2-methoxyethanol, 82 parts of hi-flash naphtha, 1.7 parts of glacial acetic acid, 0.8 parts of ammonium chloride, 1.6 parts of calcium chloride, and 39.5 parts of manganous oxide.

The autoclave was sealed and purged twice with carbon dioxide. The reaction mixture was stirred and heated to 101°–104° C. while the $CO_2$ pressure was maintained at 2 atmospheres. After 100 minutes, a vigorous reaction occurred as indicated by an increase in the temperature of the reaction mixture to 114° C. and a decrease in the pressure. The reaction mixture was cooled to 104° C. and carbon dioxide was added at a rate that would maintain the pressure at 2 atmospheres and the temperature at 101°–107° C. When the addition of carbon dioxide ended, as indicated by an increase in the pressure in the autoclave, a total of 14 parts of carbon dioxide had been added.

The reaction mixture was maintained at 101°–107° C. for an additional 90 minutes and then cold to 38° C. Filter-aid was added, and the product was filtered. There was obtained 207 parts of an overbased manganese heptanoate solution that contained 14.3% by weight of manganese.

This solution was distilled under subatmospheric pressure to yield a fluid product that contained 22% by weight of manganese.

EXAMPLE 4

A mixture of 45 parts of n-heptanoic acid, 81.5 parts of methoxyethanol, 138 parts of hi-flash naphtha, 2.3 parts of glacial acetic acid, 2.6 parts of ammonium chloride, 5.2 parts of calcium chloride, and 65 parts of manganous oxide was stirred and heated in an autoclave at 95°–100° C. under a carbon dioxide pressure of 1.5 atmospheres. After the reaction mixture had been maintained under these conditions for 90 minutes, the carbonation reaction began, as was shown by a sharp exotherm and by the rapid absorption of carbon dioxide.

The reaction mixture was maintained at 95°–100° C. and carbon dioxide was added to it at a rate that maintained the pressure at 1.5 atmospheres until there was no further abrosption of carbon dioxide. The reaction mixture was cooled, treated with filter-aid, and filtered.

There was obtained an overbased manganese heptanoate solution that contained 13.0% of manganese. The yield was 93.5%, based on the weight of manganous oxide charged, and the overbasing was 347%.

EXAMPLE 5

A mixture of 60.5 parts of n-heptanoic acid, 62 parts of 2-methoxyethanol, 123 parts of hi-flash naphtha, 3.1 parts of glacial acetic acid, 1.6 parts of ammonium chloride, 3.3 parts of calcium chloride, and 82 parts of manganous oxide was stirred and heated in an autoclave at 95°–100° C. under a carbon dioxide pressure of 2 atmospheres. After the reaction mixture had been maintained under these conditions for 150 minutes, the carbonation reaction began. The reaction mixture was maintained at 95°–100° C. under a pressure of 2 atmospheres until the carbonation reaction had been completed. It was then cooled, treated with filter-aid, and filtered.

The overbased manganese heptanoate solution obtained contained 16.6% of manganese. The yield, based on the weight of manganous oxide charged, was 94.8%, and the overbasing was 325%.

COMPARATIVE EXAMPLE

The procedure described in Example 1 was repeated except that formic acid ws omitted from the reaction mixture. The carbonation reaction did not begin until the reaction mixture had been heated at 95°–100° C. at a pressure of 2 atmospheres for 250 minutes. When the reaction had been completed, the reaction mixture was cooled, treated with filter-aid, and filtered. It filtered very poorly as compared with the products of Examples 1–5.

The overbased manganese heptanoate solution obtained contained 12.9% of manganese. The yield, based on the weight of manganous oxide charged, was 89.6%, and the overbasing was 283%.

What is claimed is:

1. In the process for the production of solutions of overbased manganese salts of organic acids that contain at least 13% by weight of manganese that comprises contacting a reaction mixture that comprises (1) excess manganous oxide, (2) an organic acid selected from the group consisting of oil-soluble organic carboxylic acids and oil-soluble sulfonic acids, (3) a promoter selected from the group consisting of ammonium halides, ammonium nitrate, mono-, di-, and trihydrocarbyl amine hydrohalides containing 1 to 3 carbon atoms, ammonim sulfide, and ammonium peroxysulfate, (4) a copromoter selected from the group consisting of alkaline earth halides, aluminum chloride, and ferric chloride, and (5) a solvent system containing from 10% to 90% by weight of an alcohol having from 1 to 12 carbon atoms and from 10% to 90% by weight of an inert solvent selected from the group consisting of hydrocarbons, halogenated hydrocarbons, and mixtures thereof with carbon dioxide at a temperature in the range of 70° C. to 120° C. at a pressure in the range of 1 atmosphere to 10 atmospheres until the carbonation is complete, the improvement that comprises carrying out the carbonation reaction in the presence of 0.5% to 5% by weight, based on the weight of the solvent system, of a third promoter that is an alkanoic acid having 1 to 3 carbon atoms.

2. The process of claim 1 wherein the carbonation reaction is carried out in the presence of 1% to 2% by weight, based on the weight of the solvent system, of the third promoter.

3. The process of claim 1 wherein the third promoter is formic acid.

4. The process of claim 1 wherein the third promoter is acetic acid.

5. The process of claim 1 wherein the reaction mixture is maintained at 90° to 110° C. at a pressure in the range of 1.5 to 3.5 atmospheres during the carbonation reaction.

6. The process of claim 1 wherein the reaction mixture comprises excess manganous oxide, heptanoic acid, ammonium chloride, calcium chloride, formic acid, methoxyethoxyethanol, and naphtha.

7. The process of claim 1 wherein the solvent system contains 25% to 40% by weight of 2-methoxyethoxyethanol and 60% to 75% by weight of naphtha.

8. The process of claim 1 wherein the solvent system contains 25% to 40% by weight of 2-methoxyethanol and 60% to 75% by weight of naphtha.

9. The process of claim 1 wherein the amount of the solvent system used is that which will produce a product that contains from 13% to 20% by weight of manganese.

10. The process of claim 1 wherein the reaction mixture contains not more than 1.50 part by weight of alcohol per part by weight of manganous oxide.

* * * * *